United States Patent [19]

Hendrick

[11] Patent Number: 5,095,278

[45] Date of Patent: Mar. 10, 1992

[54] PLANAR INTERDIGITATED DIELECTRIC SENSOR

[75] Inventor: Kendall B. Hendrick, Landenberg, Pa.

[73] Assignee: TA Instruments, Inc., New Castle, Del.

[21] Appl. No.: 373,252

[22] Filed: Jun. 29, 1989

Related U.S. Application Data

[63] Continuation-in-part of Ser. No. 274,461, Nov. 21, 1988, abandoned.

[51] Int. Cl.$^5$ ............................................. G01R 27/26
[52] U.S. Cl. ................................. 324/687; 324/689; 324/685
[58] Field of Search ............... 324/696, 721, 670, 685, 324/689, 687

[56] References Cited

U.S. PATENT DOCUMENTS

| | | |
|---|---|---|
| 3,696,360 | 10/1972 | Gajewski . |
| 3,879,644 | 4/1975 | Maltby . |
| 4,277,742 | 7/1981 | Kovac ................................ 324/689 |
| 4,423,371 | 12/1983 | Senturia et al. . |
| 4,510,436 | 4/1985 | Raymond . |
| 4,654,598 | 3/1987 | Arulanadan et al. . |
| 4,710,550 | 12/1987 | Kranbuehl . |
| 4,723,908 | 2/1988 | Kranbuehl . |

FOREIGN PATENT DOCUMENTS

| | | |
|---|---|---|
| 665303 | 6/1963 | Canada . |
| 1141809 | 12/1962 | Fed. Rep. of Germany . |
| 3416945 | 11/1985 | Fed. Rep. of Germany ...... 324/696 |
| 160355 | 6/1962 | U.S.S.R. . |

OTHER PUBLICATIONS

Society for Advancement of Material and Process Engineering Journal, vol. 19, No. 4, Jul./Aug. 1983.

Primary Examiner—Kenneth A. Wieder
Assistant Examiner—Jose M. Solis
Attorney, Agent, or Firm—Kirkland & Ellis

[57] ABSTRACT

A planar interdigitated dielectric sensor useful for measuring the surface properties of a material is disclosed. The sensor is formed on an insulating substrate. Attached to the surface of the substrate is an excitation electrode and a response electrode disposed in an interdigitated pectinate configuration and a resistance temperature device a (metallic strip). Filling the space between the electrodes and the metallic strip is an insulating material of known dielectric properties. The upper surface of the electrodes and the metallic strip are generally coplanar with respect to the insulating material between the electrodes thus forming a flat upper surface on the sensor. This flat upper surface serves to eliminate air gaps between the sensor surface and sample when analyzing relatively viscous materials.

9 Claims, 3 Drawing Sheets

PLANAR INTERDIGITATED DIELECTRIC SENSOR

CROSS-REFERENCE TO RELATED APPLICATION

This application is a continuation-in-part of application Ser. No. 07/274,461 filed Nov. 21, 1988 now abandoned.

BACKGROUND OF THE INVENTION

This invention relates to a sensor which can be used to measure dielectric properties of materials.

It is well known that by measuring dielectric properties of a sample as a function of temperature, valuable information can be gained concerning the physical and chemical properties of the sample.

Two techniques are commonly used to measure dielectric properties. For many years measurements have been made by placing a sample between parallel plate electrodes, applying an electrical signal in the form of an alternating voltage to one of the electrodes (i.e. the excitation electrode) and measuring the electrical signal from the other electrode (i.e. the response electrode). The following equation is used:

$$C = e_o e' \frac{A}{d} \text{ where}$$

c = capacitance
$e_o$ = permittivity of free space (a constant)
$e'$ = permittivity of sample (being measured)
A = area of parallel plate response electrode
d = distance between the excitation and response electrode plates By measuring capacitance, the permittivity of the sample can be easily calculated if the area of the parallel plate electrode and the distance between the excitation and response electrodes are known. A device for making measurements in this manner is disclosed in copending application Ser. No. 07/206,092. This technique is primarily used to characterize bulk properties of a material in that the signal is monitored through the entire thickness of the material. This technique has several limitations. Often times thick samples are of interest to be analyzed. In the parallel plate technique, the signal to noise ratio decreases as a function of increasing distance between the electrode plates. Larger plates could be utilized to increase the area thereby increasing the signal however there does exist a practical limitation.

Many times the surface of a material is to be analyzed. In polymer molding, skin effects are of interest due to faster cooling of the materials surface than its interior. The chemical and mechanical properties of the surface of the material are more indicative of its end use properties than the bulk interior properties. Coatings on a material surface are also of interest in dielectric analysis. Paints, adhesives, and copolymers often require analysis. A parallel plate measurement would detect the properties of the coating and its associated substrate in a bulk fashion. It is impossible to analyze surface characteristics by parallel plate analysis.

An alternate technique was developed and is commonly known which addresses the limitations of the parallel plate measurement. An interdigitated combed electrode is commonly used for obtaining dielectric measurements on surfaces of materials and fluids. Probes of this type have been used for many years as moisture detection devices. Gajewski U.S. Pat. No. 3,696,360, discloses an interdigited electrode for moisture sensing. In the past few years these interdigitated probe structures were adapted to measure dielectric properites of materials. See, *Society for the Advancement of Material and Process Engineering Journal,* Volume 19, No. 4, July/August, 1983.

In this technique a sample is placed on the electrode surface, an electrical signal is applied to one "finger" of the interdigitated fingers or combs of the electrode array, and the signal is measured at the other finger of the array. These two fingers are termed excitation and response electrodes respectively. In this fashion the signal only penetrates the surface of the material. The penetration depth is approximately equal to the distance separating the fingers in the interdigitated electrode array. This technique is ideal for monitoring the dielectric characteristics of fluids, curing systems, adhesives, and relatively low viscosity materials. This technique, however, has severe limitations when analyzing films, hard plastics, and pre-cured systems (i.e., relatively viscous materials).

Problems arise due to surface contact with these types of materials. Interdigitated surface electrodes are inherently quite sensitive to whatever material contacts the surface, including air. Air gaps can severely limit the ability to measure dielectric properties of a material effectively since air and vacuum have the lowest permittivity theoretically possible ($e'$vac = 1.00000). Thus, air gaps on the electrode surface will significantly depress the measurement of a material's permittivity. Air also induces noise in the capacitance measurement. Unfortunately all electrode materials used in the fabrication of these surface sensors have a finite height or thickness. Obviously, a hard material will bridge the electrode fingers of the sensor. This bridge traps air between the electrode surface and the material in the spaces between the electrode fingers. This causes the measured permittivity to be the average value of the material's permittivity and the permittivity of air. This effect can depress the correct measurement of permittivity by as much as 50%.

Primarily dielectric measurements are made as a function of temperature to assess the characteristics of a material. As these viscous materials are heated beyond the glass-transition region they begin to flow and displace the air between the electrode fingers. This results in a dramatic elevation in the permittivity measurement. It would seem a viable option prior to analysis to preheat materials so that they "flow out" to fill the air gaps on the electrode to address this problem. Unfortunately, most materials change their molecular structure upon heating and cooling. This change effects the accurate measurement of glass transition temperature, degree of crystallinity, degree of cure, and most importantly, permittivity. Unfortunately the amount of air present between the electrode surface and the material being analyzed changes as the material softens with temperature. If the amount of air in this space remained constant a calibration could be made and the measurement could be corrected.

Accurate measurements of sample temperatures obviously are also important since dielectric measurements are normally monitored as a function of temperature. In some dielectric analyzers, a thermocouple is placed as close to the edge of the sample and plate as possible without contact, and the sample temperature is assumed to be that of the thermocouple. Obviously, this temperature measurement is not as accurate as measuring the temperature of the sample directly. In at least one single surface sensor, it is known to incorporate a thermal diode in the electrode. See, Micromet product literature in the Information Disclosure Statement-Option S-1 integrated circuit dielectric sensor for use in the Micromet Eumetric System II microdielectrometer. However, thermal diodes are limited to a temperature of 200° C. and are not as accurate as temperature sensors in direct contact with the sample.

A surface analysis dielectric sensor is needed to eliminate the above mentioned limitations of existing interdigitated pectinate probes for use with relatively viscous materials.

SUMMARY OF THE INVENTION

Provided by this invention is an surface analysis dielectric sensor with the following improvements:

(a) an interdigitated, combed electrode configuration supported on an insulating substrate;

(b) a surface being generally planar and flat to within microns, thereby eliminating air gaps between the surface of the electrode and any material of interest;

(c) an embodiment which allows accurate dielectric measurements over an extreme temperature range; and (d) temperature sensing means comprising a metallic strip, preferably platinum, which is adhered to the surface of the sensor.

DETAILED DESCRIPTION

Figure 1:
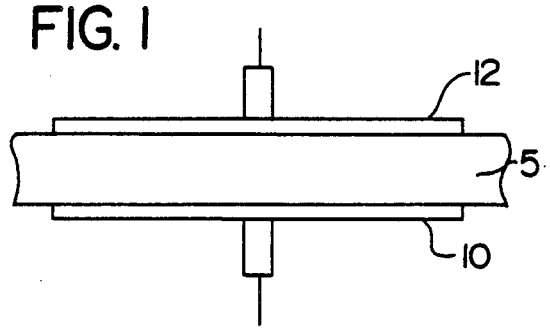
FIG. 1 is a schematic describing a parallel plate sensor configuration of the prior art with sample.
Figure 2:
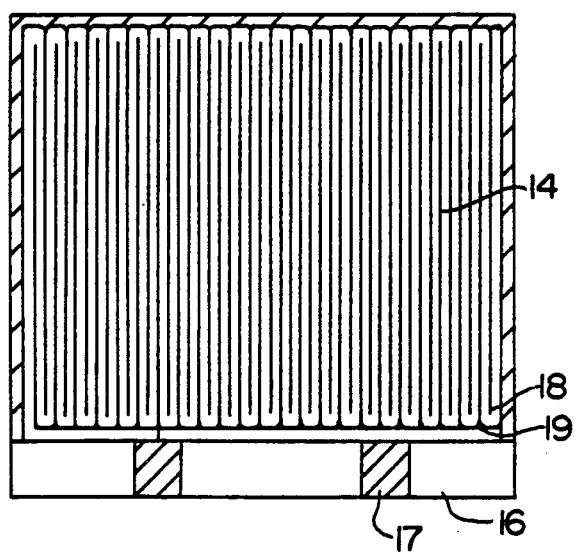
FIG. 2 is a top view of an interdigitated pectinate sensor of the prior art.
Figure 3:
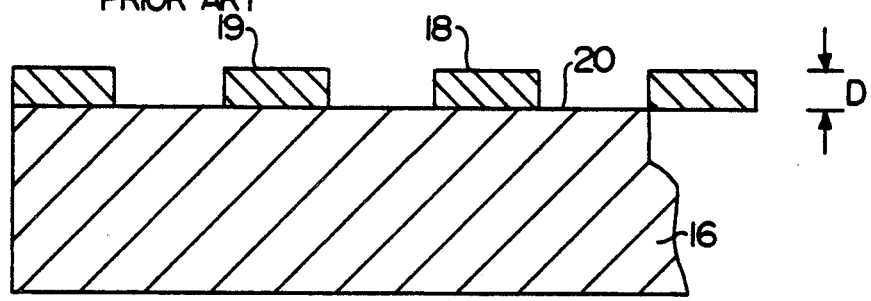
FIG. 3 is a side elevational view of surface dielectric sensors of the prior art.
Figure 4:
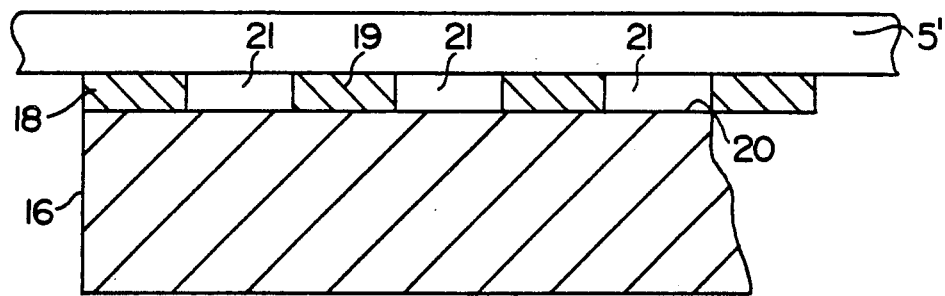
FIG. 4 is a side elevational view which shows a sample bridging the surface sensor of the prior art.

Referring now to the drawing in FIG. 1, the schematic shows a typical parallel plate arrangement wherein the sample S is sandwiched between an excitation electrode plate 10 and a response electrode plate 12. As discussed in the background, only the bulk characteristics of a material can be analyzed in this technique. FIG. 2 shows a surface analysis sensor of the prior art. The interdigitated array 14 is made up of two combed shaped electrodes disposed in a pectinate configuration. One such electrode being the excitation electrode 18, and the other electrode being the response electrode 19. These electrodes are connected to electrode contacts 17, and are supported on an insulating substrate 16. FIG. 3 is a cross-section of the sensor described in FIG. 2. As can be readily seen the electrodes 18 and 19 extend a distance D above the surface 20 of the substrate 16. FIG. 4 shows a relatively viscous sample S' under analysis with the sensor of FIGS. 2 and 3. As is shown, unavoidable air gaps 21 are created as the sample S' bridges the electrode fingers 18 and 19 since the sample S' does not readily flow.

Figure 5:
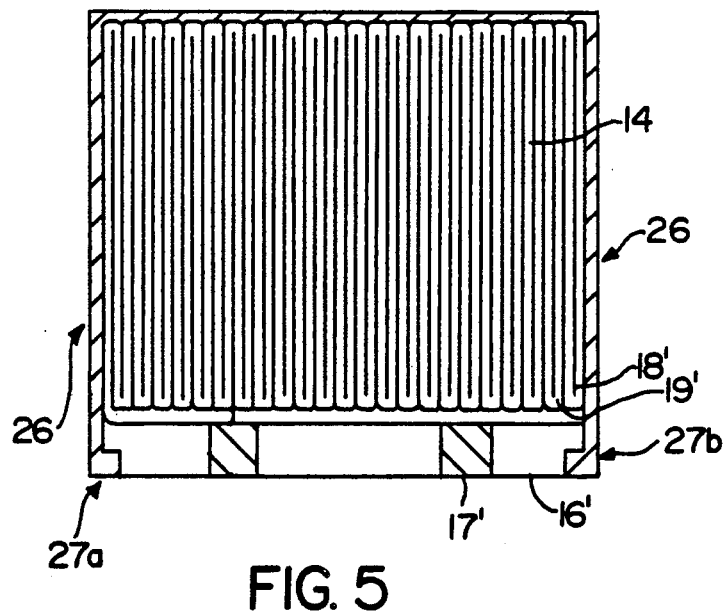
FIG. 5 is a top view of an interdigiated pectinate sensor of our invention.

FIG. 5 shows a top view of the sensor of the present invention. From this view it is easy to see metallic strip 26, preferably platinum, adhered to the surface of the sensor and running around the perimeter of the sensor but not in contact with interdigitated electrode array 14'. At the end points of metallic strip 26 are electrical contact points 27a and 27b. Metallic strip 26 serves as a resistance temperature device. It is a well known principle that by measuring the resistance of a metal, the temperature of the metal can be determined. Since metallic strip 26 is in direct contact with the sample it gives a very accurate temperature measurement of the sample.

Figure 6:
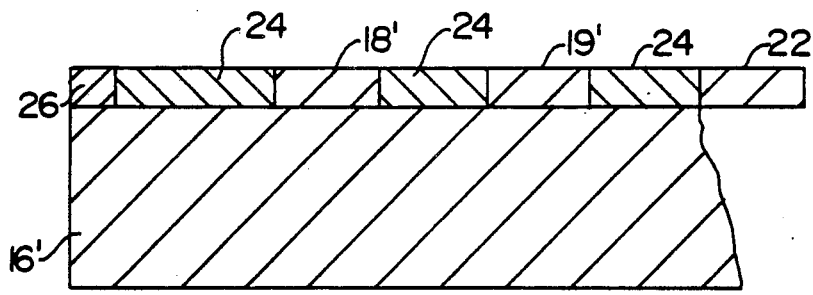
FIG. 6 is a side elevational view of the present invention.
Figure 7:
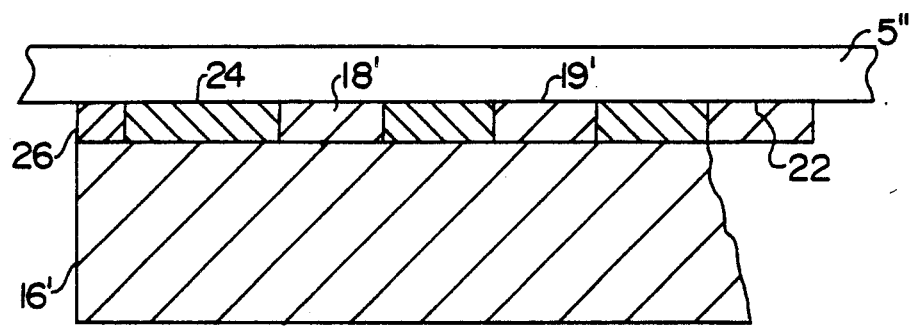
FIG. 7 is a side elevational view of a sample under analysis with the present invention.
Figure 8:
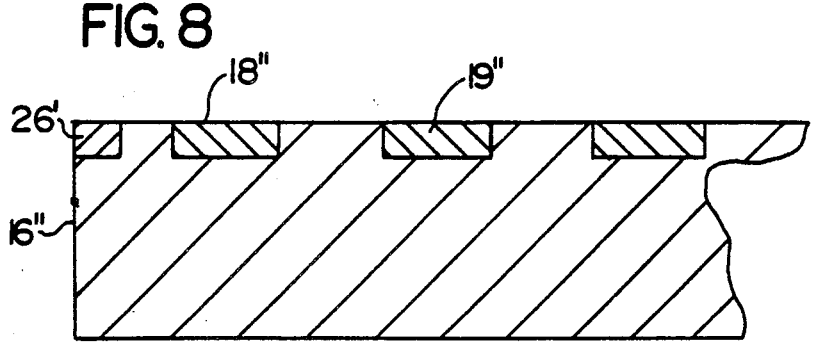
FIG. 8 is a side elevational view of present invention manufactured by an alternate method.

The view from FIG. 5 does not show that the sensor is planar. However, this is evident from FIG. 6 which is a partial side elevational view of FIG. 5. From this view it is evident that surface 22 of the sensor is generally planar and flat. The voids between the excitation electrode 18', the response electrode 19' and metallic strip 26 contains a dielectric material 24 with known dielectric properties. FIG. 7 shows a sample S" under analysis with the sensor of FIG. 6. As is shown, no air gaps exist between the sensor surface and the sample being analyzed.

The substrate 16' of our invention is any of a number of insulating materials, well known to those skilled in the art such as polyimide film, ceramic, or glass. The electrodes 18' and 19' of our invention are metallic. As described above these electrodes are combed-shaped and disposed in an interdigitated pectinate configuration. These electrodes are attached to the upper surface of the insulating substrate 16'. The electrodes 18' and 19' have a finite height and a flat upper surface. These metallic electrodes are conductors such as gold, platinum, copper, palladium, and so forth. Likewise, metallic strip 26 also has a finite height (the same height as electrodes 18' and 19') and a flat upper surface.

The dielectric material 24 with known dielectric properties between the electrodes is an insulating glass such as those commonly used in the manufacture of thick film hybrid circuits. One such insulating glass is manufactured by E.I. du Pont de Nemours and Company as thick film dielectric composition No. 5034 or No. 5042.

There are at least two basic manufacturing methods which can be used to manufacture the sensor of the present invention. Thick film hybrid technology using screen printing processes is known in the art and can be used to form the electrode array, as well as to selectively fill the spaces between the electrodes. A flat generally planar surface is obtained by filling the spaces between the electrodes and the resistance temperature device with excess dielectric insulating material. The sensor is then lapped to the desired surface flatness. Another method of manufacturing the sensor of the present invention utilizes etching technology. In this method grooves are etched by chemical or mechanical means into the surface of the substrate. The grooves are combed-shaped and disposed in an interdigitated pectinate configuration. The grooves are then filled with the metallic conductors. A sensor obtained using this method is shown in FIG. 7. In this configuration, the insulating material between the excitation electrode 18″, the response electrode 19″ and metallic strip 26′ consists of the substrate 16″ itself.

Many alternate manufacturing methods would be obvious to one skilled in the art.

I claim:

1. A planar interdigitated dielectric sensor useful for measuring surface properties of a material comprising:
   (a) an insulating substrate;
   (b) a metallic excitation electrode attached to the surface of said substrate, the excitation electrode being comb-shaped and having a planar upper surface;
   (c) a metallic response electrode attached to the surface of said substrate, the response electrode being comb-shaped, having a planar upper surface coplanar with said planar upper surface of the excitation electrode and interdigitatedly positioned with respect to said excitation electrode;
   (d) a resistance temperature device which is a metallic strip attached to the surface of said substrate, said metallic strip having a planar upper surface that is coplanar with said planar upper surface of the excitation electrode and the planar upper surface of said response electrode; and
   (e) an insulating glass with known dielectric properties attached to the surface of the substrate, filling the spaces between the excitation electrode, the response electrode and the metallic strip, having a planar upper surface coplanar with respect to the coplanar upper surfaces of said excitation electrode, said response electrode and the metallic strip, whereby the upper surfaces of the excitation electrode, the response electrode, the metallic strip and the insulating glass are adapted for placement against a surface of a viscous material that is being tested such that no air gaps are present between said upper surfaces and the surface of the viscous material.

2. The sensor of claim 1 wherein the resistance temperature device is comprised of platinum.

3. A planar interdigitated dielectric sensor useful for measuring surface properties of materials comprising:
   (a) an insulating substrate having a planar upper surface, said upper surface containing a first recessed groove having a comb-like shape and a second recessed groove also having a comb-like shape, said first and second grooves being positioned interdigitatedly, and a third recessed groove being positioned around the perimeter of said first and second recessed grooves;
   (b) a metallic response electrode with a planar upper surface positioned within said first groove, said planar upper surface of the response electrode being coplanar with respect to the upper surface of said substrate;
   (c) a metallic excitation electrode with a planar upper surface positioned within said second groove, said planar upper surface of the excitation electrode being coplanar with respect to the upper surface of said substrate;
   (d) a resistance temperature device which is a metallic strip with a planar upper surface positioned within said third recessed groove, said planar upper surface of the metallic strip being coplanar with respect to the upper surface of said substrate, whereby the upper surfaces of the excitation electrode, the response electrode, the metallic strip and the substrate are adapted for placement against a surface of a viscous material that is being tested such that no air gaps are present between said upper surfaces and the surface of the viscous material.

4. The sensor of claim 3 wherein the resistance temperature device is comprised of platinum.

5. The planar interdigitated dielectric sensor of claim 1, wherein the surfaces of the excitation electrode, the response electrode, the metallic strip and the insulating glass are coplanar and flat within microns.

6. The planar interdigitated dielectric sensor of claim 1, wherein the electrodes are chosen from a group consisting of gold, platinum, copper, and palladium.

7. The planar interdigitated dielectric sensor of claim 3, wherein the surface of the excitation electrode, the response electrode, and the substrate are coplanar and flat within microns.

8. The planar interdigitated dielectric sensor of claim 3, wherein the substrate is a dielectric material with known dielectric properties.

9. The planar interdigitated dielectric sensor of claim 3, wherein the electrodes are chosen from a group consisting of gold, platinum, copper, and palladium.

* * * * *